(12) United States Patent
Leoni et al.

(10) Patent No.: US 8,840,222 B2
(45) Date of Patent: Sep. 23, 2014

(54) TECHNIQUES RELATED TO SATELLITE AEROSOLS

(71) Applicant: Hewlett-Packard Development Company, L.P., Houston, TX (US)

(72) Inventors: Napoleon J Leoni, Palo Alto, CA (US); Henryk Birecki, Palo Alto, CA (US); Omer Gila, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 188 days.

(21) Appl. No.: 13/631,547

(22) Filed: Sep. 28, 2012

(65) Prior Publication Data

US 2014/0092174 A1    Apr. 3, 2014

(51) Int. Cl.
    *B41J 29/393*    (2006.01)
(52) U.S. Cl.
    USPC .......................................................... 347/19
(58) Field of Classification Search
    None
    See application file for complete search history.

(56) References Cited

U.S. PATENT DOCUMENTS

| | | | |
|---|---|---|---|
| 3,949,390 A | 4/1976 | Rayl et al. | |
| 6,435,672 B1 * | 8/2002 | Groninger et al. | 347/69 |
| 6,688,729 B1 * | 2/2004 | Imanaka et al. | 347/48 |
| 6,948,637 B1 * | 9/2005 | Jacobs | 222/174 |
| 7,031,133 B2 | 4/2006 | Riebel et al. | |
| 7,600,849 B2 * | 10/2009 | Bibl et al. | 347/19 |
| 7,812,306 B2 | 10/2010 | Fissan et al. | |
| 2010/0282361 A1 | 11/2010 | Peters | |
| 2011/0051153 A1 | 3/2011 | Gila et al. | |
| 2011/0216126 A1 | 9/2011 | Lee | |
| 2012/0019589 A1 | 1/2012 | Gila et al. | |

FOREIGN PATENT DOCUMENTS

| | | |
|---|---|---|
| DE | 4008348 | 9/1991 |
| JP | 2008183839 | 8/2008 |
| JP | 2010208194 | 9/2010 |
| WO | WO-2010114534 | 10/2010 |
| WO | WO-2011090487 | 7/2011 |

OTHER PUBLICATIONS

U.S. Appl. No: 13/098349; Filed Apr. 29, 2011; Apparatus to Capture Aerosols, Fluid Jetting Apparatus, and Aerosol Diverters.
Evaluation of Ultrafine Particle Emissions From Laser Printers Using Emission Test Chambers, http://pubs.acs.org/doi/abs/10.1021/es702426m > on Page(s): 4338-4343; Volume: 42.

* cited by examiner

Primary Examiner — Lamson Nguyen

(57) ABSTRACT

Examples described herein illustrate techniques related to satellite aerosol generation. In some examples, aerosols are sensed based on the interaction between satellite aerosols and a corona discharge from a corona source.

20 Claims, 8 Drawing Sheets

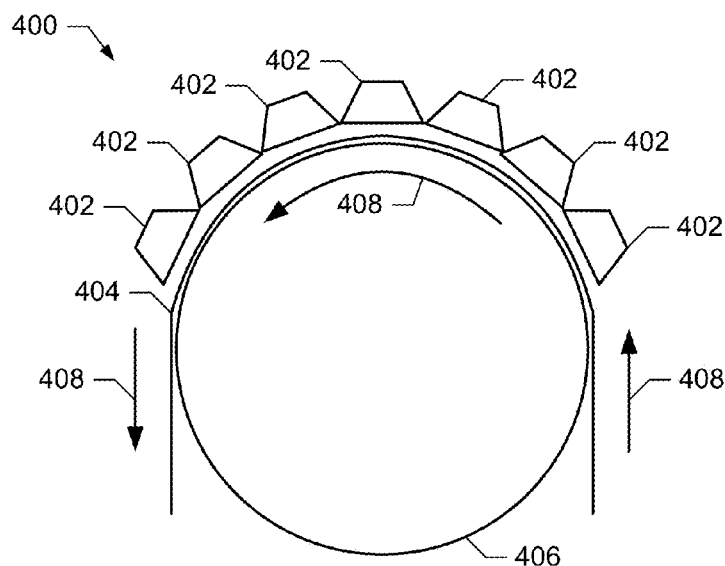
FIG. 4A
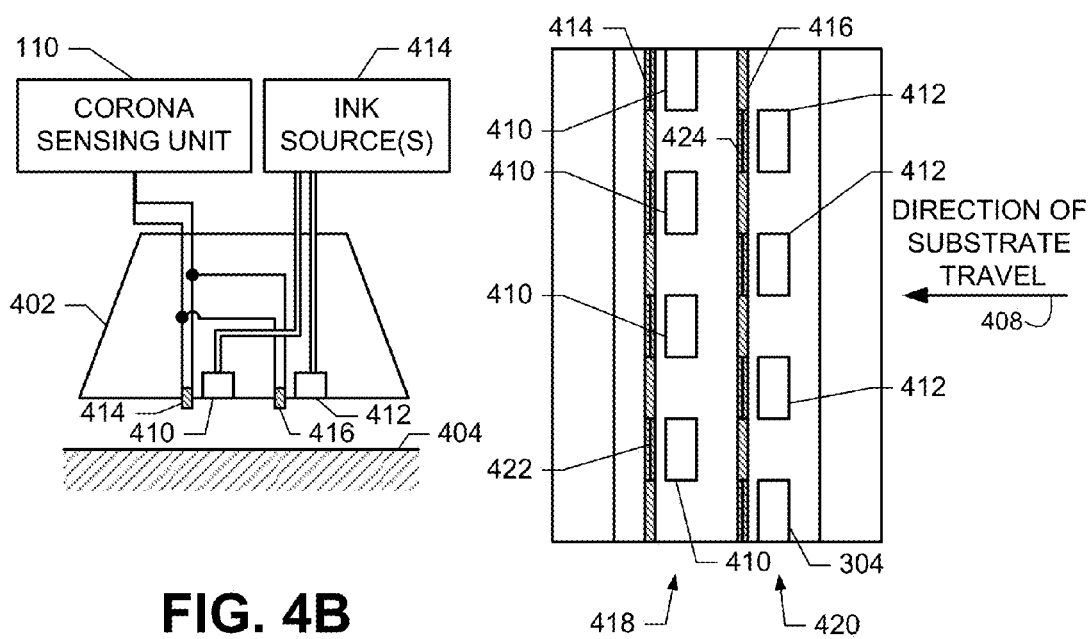
FIG. 4B
FIG. 4C

716 — PROCESSOR

802 — MEMORY
- REGULATION MODULE — 804
- CORONA SENSING MODULE — 806

OPERATION OF FLUID EJECTION SYSTEM

902 — GENERATION OF CORONA DISCHARGE WITHIN FLUID EJECTION SYSTEM

904 — EJECT DROPLETS OF THE FLUID TOWARDS A RECEPTION REGION, WHEREBY, SATELLITE AEROSOLS CAN ORIGINATE FROM THE FLUID DROPLETS

906 — MEASURE CORONA DISCHARGE PARAMETER ASSOCIATED WITH VARIATION OF CORONA DISCHARGE

908 — DETERMINE MAGNITUDE OF AEROSOL SATELLITE GENERATION FROM DROPETS OF INKS BASED ON MEASURED CORONA DISCHARGE PARAMETER

FIG. 9

1000
DETERMINATION OF MAGNITUDE OF AEROSOL SATELLITE GENERATION

1002
GENERATE CORONA DISCHARGE IN MEASUREMENT AREA BY IMPOSING CORONA VOLTAGE BETWEEN CORONA SOURCE AND CORONA GROUND

1004
REGULATE CORONA DISCHARGE TO MAINTAIN CONSTANT CORONA CURRENT

1006
SENSE AEROSOLS IN MEASUREMENT AREA BASED ON REGULATION PARAMETER

TECHNIQUES RELATED TO SATELLITE AEROSOLS

BACKGROUND

Ejection of fluid droplets on a reception region using a fluid ejection device including nozzles is a useful approach for digitally dispensing a fluid. Examples of such fluid ejection devices include inkjet printing systems for reproducing an image pattern on a substrate (e.g., paper or other media). Other examples include dosing systems for digitally dispensing fluids into assay plates for drug discovery. Such dosing systems may be built similarly as an inkjet printhead. The HP D300 Digital Dispenser is an example of such digital dispensers.

Ejection of fluid droplets may cause generation of contamination particles due to satellites formed from ejected droplets. For example, in inkjet printers, the jetting of ink drops may result in the formation of satellites of the ink.

Such satellites may uncontrollably contaminate the target regions towards which droplets are being ejected (e.g., a print media onto which ink is ejected to print an image pattern or a titration plate). Satellite contamination may require servicing the fluid ejection device. Moreover, satellites may cause damage to nozzles or other equipment of fluid ejection devices.

BRIEF DESCRIPTION OF THE DRAWINGS

In order that the present disclosure may be well understood, various examples will now be described with reference to the following drawings.

FIG. 4A to 4C show schematically portions of an inkjet web press according to examples.

FIG. 8 shows a computer readable medium according to examples.

FIG. 9 shows a process flow for operating fluid ejecting systems according to examples.

FIG. 10 shows a process flow for sensing aerosols according to examples.

FIG. 11 shows a graph illustrating variation over time of various corona regulation parameters according to examples.

DETAILED DESCRIPTION

Figure 1:
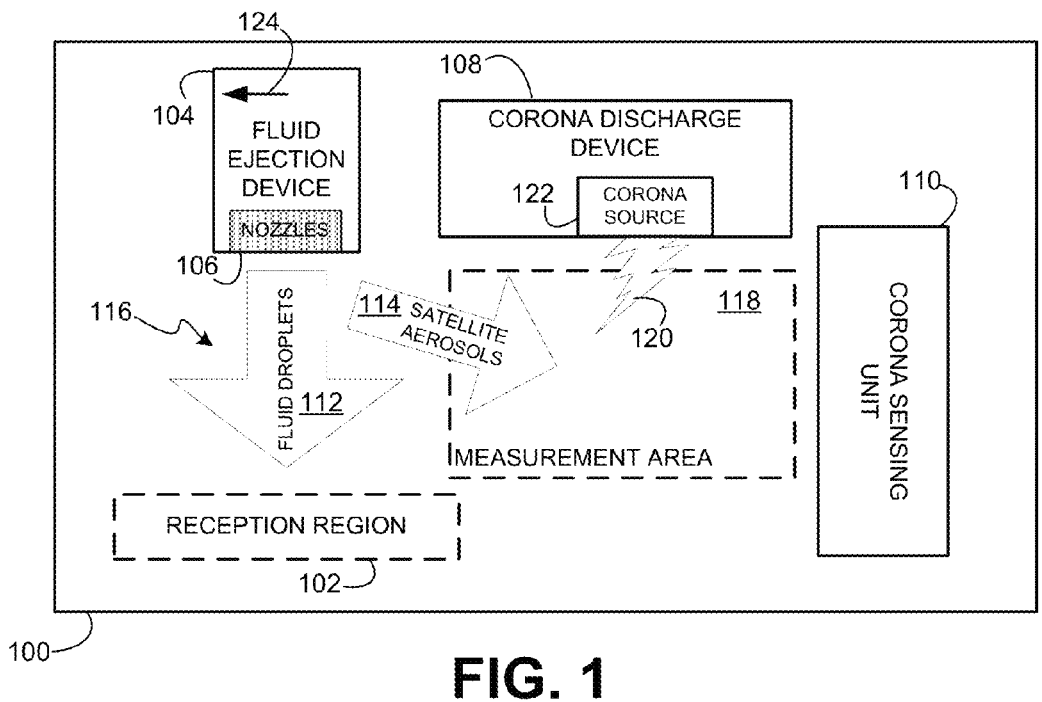
FIG. 1 shows a block diagram of a system for ejecting a fluid according to examples.

In the following, numerous details are set forth to provide an understanding of the examples disclosed herein. However, it will be understood that the examples may be practiced without these details. Further, in the following detailed description, reference is made to the accompanying figures, in which various examples are shown by way of illustration. While a limited number of examples are illustrated, it will be understood that there are numerous modifications and variations therefrom.

In this regard, directional terminology, such as "top," "bottom," "front," "back," "left," "right," "vertical," etc., is used with reference to the orientation of the figures being described. Because disclosed components can be positioned in a number of different orientations, the directional terminology is used for purposes of illustration and is in no way limiting. In the drawings, the dimensions of layers and regions are exaggerated for clarity of illustration.

As set forth above, droplet satellites may be generated during operation of fluid ejection systems. Droplet satellites may have a sufficient mass and momentum to land on the reception region (i.e., the regions towards which fluid droplets are aimed to). Smaller satellites may not have a sufficient mass and momentum to land on the reception region. This latter population of smaller satellites is commonly referred to as satellite aerosols or mist (i.e., aerosol droplets). Further, fluid ejection systems may operate by translating either a fluid ejection device or a substrate onto which droplets are aimed to, in order to implement spatial addressability of the fluid being ejected. Such translations may result in air flow during system operation. Satellite aerosols may be entrained in the air flow, thereby creating a potential for causing contamination of surfaces of system components downstream of the fluid deposition zone. Hence, satellite aerosol generation may negatively affect productivity of the fluid ejection device. Monitoring aerosol generation might be useful to assess condition of the fluid ejection system.

Examples described herein illustrate techniques to sense satellite aerosol generation caused by a fluid ejection device based on the interaction between satellite aerosols and a corona discharge. Further, in some examples, sensing of aerosols is also illustrated. Satellite aerosol detection via corona discharge facilitates a relatively simple implementation and may be implemented using components at a relatively low cost without sacrificing sensing capability.

Conventional solutions for sensing aerosols include laser particle size spectrometers (e.g. Topas LAP 322) or aerosol mass collection approaches (e.g. Kanomax Piezo Balance). Some of these conventional methods require suction of the aerosols into a detection zone. In contrast thereto, at least some examples described herein do not require such suction. Suction may be particular difficult to be implemented in some systems, e.g. when satellite aerosols are entrained in a located air flow caused by translation of system components. Further, conventional solutions may be limited to very low aerosol concentration (for example $10^4$ particles/$cm^3$ for some laser approaches and 10 mg/$m^3$ for some piezo balance approach). Moreover, at least some conventional solutions require dilution of the satellite aerosols. At least some examples described herein do not require dilution, as the sensing signal (related to interaction between satellite aerosols and corona discharge) actually increases with the aerosol concentration, while providing high sensibility to low aerosol concentrations.

Although some of the examples below are illustrated with respect to printing systems, techniques described herein are not limited to satellite aerosols generated by a printing system, but might be implemented in other systems for dispensing liquid substances such as, but not limited to, dosing systems including a fluid ejection device to eject droplets of a dosed fluid. For example, such a dosing system may implement digital dispensing for drug discovery that include a fluid ejection device for selectively dispensing drugs into a titration plate.

FIG. 1 is a block diagram of a system 100 for ejecting a fluid on a reception region 102. System 100 includes a fluid ejection device 104, a corona discharge device 108, and a corona sensing unit 110.

Fluid ejection device 104 includes a plurality of nozzles 106 to eject fluid droplets 112 towards reception region 102. More specifically, fluid ejection device 104 is to eject fluid droplets 112 into a fluid deposition zone 116. Fluid ejection device 104 may be movable in order to implement addressability of fluid deposition. In the Figures, a single fluid ejection device is illustrated. It will be understood that the number of fluid ejection devices depend on the specific design constraints of the fluid deposition system. As illustration, for color printing applications, a fluid ejection device may be provided for each ink type. For example, a printer may include four fluid ejection devices, one for black ink, one for cyan ink, one for magenta ink, and one for yellow ink.

Further, it will be understood that the number of nozzles per fluid ejection device and the dimensions of the nozzles vary depending upon desired design constraints (e.g., desired droplet size). For example, nozzles 106 may have a diameter of 30 microns allowing for the ejection of droplets of about 10 picoLiters (PL), depending upon many parameters in addition to nozzle diameter, such as chamber dimensions, ejection energy, fluid viscosity and so on.

Fluid ejection device 104 may include further components for effecting fluid droplets ejection, which are not further illustrated for the sake of clarity. Such components may enable fluid ejection using different mechanisms such as thermal jetting or piezoelectric jetting.

During system operation, satellite aerosols 114 can originate from fluid droplets 112. In particular, fluid droplets 112 may individually have an elongated shape as they are ejected from nozzles 106 due to adhesion forces between the ejected fluid and nozzles 106. The heads of fluid droplets 112 may move at a faster rate away from fluid ejection device 104 compared with the tail portions of the droplets. Thereby, satellites may lose their initial speed and break away from the droplets. Satellite aerosols 114 are relatively small and light as compared with the ejected droplets 112 and may remain suspended in a region of air adjacent to reception region 102 and fluid ejection device 104 while droplets 112 continue to move downward to reception region 102.

Satellite aerosols 114 may enter an area 118 adjacent to corona discharge device 108 and in the proximity of fluid ejection device 104. (Area 118 is hereinafter referred to as measurement area 118.) Satellite aerosols may enter measurement area 118 due to different mechanisms. For example, fluid ejection device 104 and corona discharge 108 may be mounted onto a movable carriage (not shown) that moves during printing along a scanning direction for addressing fluid ejection; satellite aerosols 114 may remain suspended downward of fluid ejection device 104, thereby entering into measurement area 118. In other examples, fluid droplets 112 are aimed to a moving substrate; substrate movement may cause an air flow that induces movement of satellite aerosols 114 into measurement area 118 (such examples are illustrated below with respect to FIG. 2).

As illustration, fluid droplets 112 may individually have a diameter of approximately 12-50 microns and a volume between 1 to 50 pL. Satellites may individually have a diameter of approximately 1-10 microns and a volume of approximately 0.01 to 0.3 pL.

Figure 2:
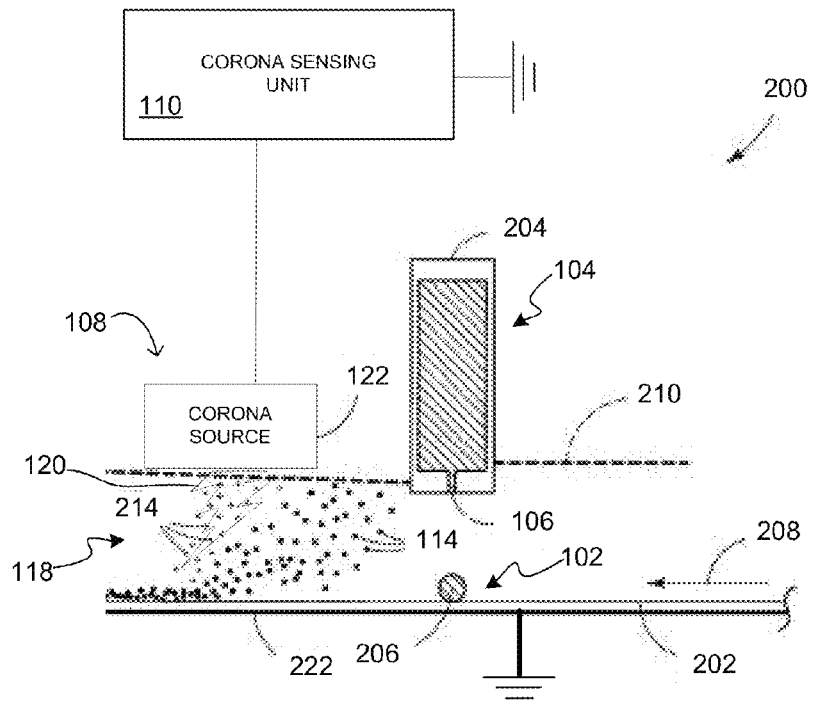
FIG. 2 shows a block diagram of a printing system according to examples.
Figure 3:
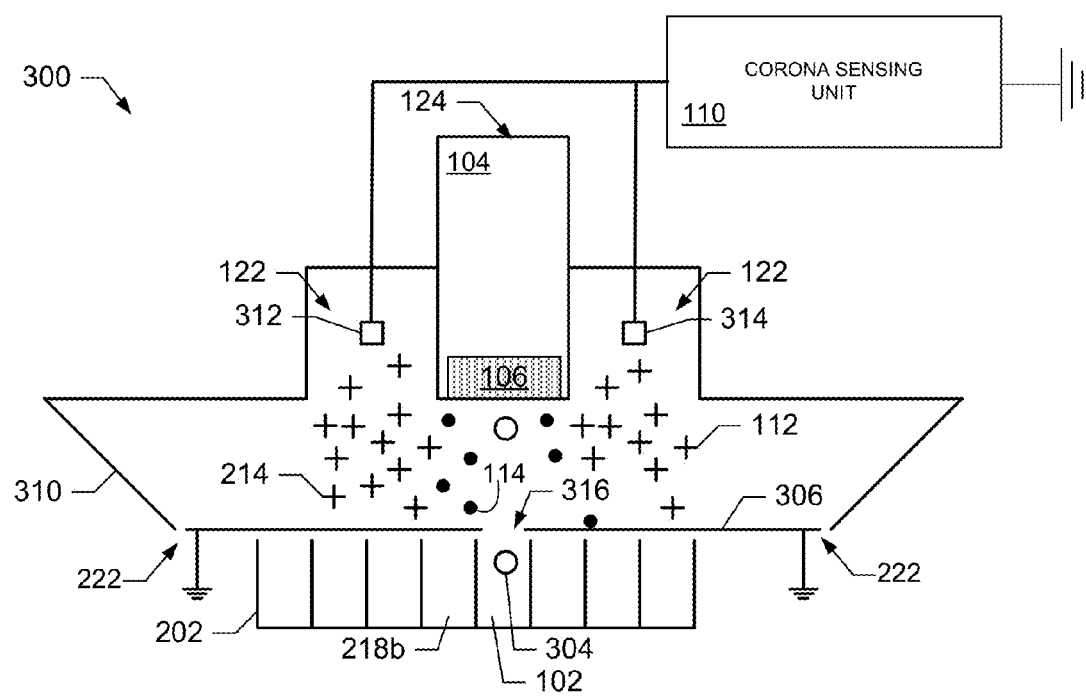
FIG. 3 shows a block diagram of a dosing system according to examples.

Reception region 102 corresponds to a region of system 100 configured to receive the element onto which fluid is to be deposited. In examples related to printing systems, reception region 102 may be a print substrate placement, which is configured to receive a substrate as illustrated in FIG. 2. In examples related to digital dispensers for drug discovery, reception region 102 may be at an essay plate placement area, which is configured to receive an essay substrate as illustrated in FIG. 3.

Corona discharge device 108 is to provide a corona discharge 120 from a corona source 122 into measurement area 118. Corona source 122 may be constituted by a conductive element suitable to induce a corona discharge into measurement area 118. Specific examples of corona sources are illustrated below with respect to FIGS. 3 to 6. A corona discharge refers to the electrical discharge brought on by the ionization of a fluid (e.g., air) surrounding a conductor (e.g., a metal wire) that is electrically energized. For example, corona source 122 may be to induce a stream of positively charged ions towards a corona ground (not shown in FIG. 1; see FIG. 2 or 3) during operation of system 100. It will be understood that there are a variety of options for implementing a corona source such as a corona wire or a corona needle. Some specific examples are illustrated below.

Corona discharge device 108 may include further components for causing corona discharge, which are not further illustrated for the sake of clarity. Such components may include, but are not limited to, a voltage generator and electric circuitry for energizing corona source 122.

Corona sensing unit 110 is to sense satellite aerosols generation caused by the fluid ejection device based on the interaction between satellite aerosols and the corona discharge. The interaction between satellite aerosols and the corona discharge causes a variation in the corona discharge. For example, corona discharge 120 may result on an ion current flow in measurement area 118; satellite aerosols 114 entering into measurement area 119 may interact with the ion flow decreasing ion mobility. This variation of corona discharge is used by corona sensing unit 110 to sense aerosols. Sensing unit 110 may be constituted by any arrangement suitably to detect a signal related to aerosol-corona interaction and process this signal in order to provide a signal indicative of satellite aerosols generation. Some specific arrangements are discussed in the following.

In examples, sensing unit 110 may be implemented as hardware or as a combination of hardware and programming. For example, sensing unit 110 may be implemented as an analog circuitry configured to sense satellite aerosol generation caused by the fluid ejection device. In other examples, sensing unit 110 may digitally process signals for sensing satellite aerosol generation. Such examples are illustrated below with respect to FIGS. 7 and 8.

Sensing unit 110 may be implemented as hardware components directly or indirectly connected to corona discharge device 108 for accessing a signal associated with the interaction between satellite aerosols and the corona discharge. For example, corona discharge device 108 may be connected to an associated circuitry (not shown in FIG. 1; see FIG. 4 for an example) for electrically energizing corona source 122. The current in the circuitry is related to the corona discharge. More specifically, the decrease in the ion flow caused by interaction between satellite aerosols 114 and corona discharge 120 as well as a screening of the corona voltage may result in a decrease of the current flowing in the associated circuitry. In an specific implementation, sensing unit 110 may include i) a probing element for accessing a corona current, ii) an analog ammeter for providing a reading of the corona current, and iii) an analog output to provide a signal related to satellite aerosol generation. This output signal may be proportional to the corona current.

In some examples, system 100 is configured to regulate the corona discharge so as to maintain constant corona current of the corona discharge. In an example, a closed-loop control is implemented for the corona current. In such a closed-loop control, the corona voltage applied between corona source 122 and a corona ground (not shown in FIG. 1) can be monitored. The monitored corona voltage can then be used as sensing variable for maintaining constant corona current of the corona discharge. In such examples, sensing unit 110 may be connected to a regulating unit and sense satellite aerosol generation based on a regulation parameter (e.g., the monitored voltage, corona current fluctuations, and/or a current imbalance between the corona source and the corona ground). Further details on corona discharge regulation and sensing based on regulation parameters are set forth below.

Figure 12:
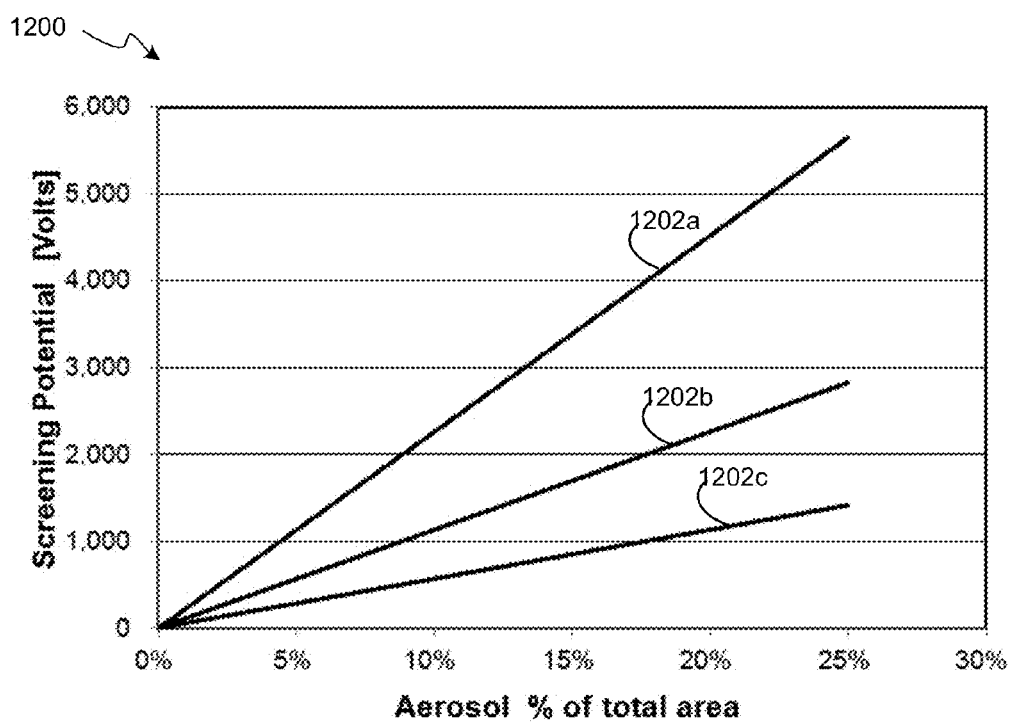
FIG. 12 shows a graph illustrating relationship between the percentage of area covered by an aerosol and corona screening potential.

Sensing unit 110 may also be configured to determine the magnitude of satellite aerosol generation. For example, the magnitude of satellite aerosol generation can be quantified from variations in the corona current or other parameters such as illustrated below with respect to FIGS. 10 to 12. Magnitude of satellite aerosol generation may include an explicit quantification of satellite aerosol generation, such as a number of satellite aerosol particles being generated. In other examples, magnitude of satellite aerosol generation may include a level of aerosol generation (e.g., low, medium, or high). In other examples, magnitude of satellite aerosol generation may include values of parameters directly related to satellite aerosol (e.g., corona voltage or current imbalance as illustrated in FIG. 11).

FIG. 2 illustrates examples herein in which the fluid ejection system is a printing system. More specifically, FIG. 2 schematically shows a portion of a printing system 200 for printing an image pattern on a substrate 202. In the example, fluid ejection device 104 includes an inkjet printhead 204. FIG. 2 further illustrates a droplet 206 ejected from inkjet printhead 204 at reception region 102. Droplet 206 is ejected trough nozzles 106 of inkjet printhead 204.

As illustrated by FIG. 2, measurement area 102 may be at a boundary layer 210 of air flow contiguous to the substrate. More specifically, printing system 200 may generate an air flow by translating substrate 202 during printing. Printing system 200 is configured to form images upon substrate 202 travelling along a substrate path 208 as shown. The movement of substrate 202 travelling along substrate path 208 generates air boundary 210. Air boundary 210 generally corresponds to a boundary where air below the boundary moves with substrate 202 in its direction of travel along substrate path 208. Generally, air above boundary 210 is not significantly affected by the travelling substrate. The height of boundary 210 generally depends of a number of parameters such as substrate velocity or substrate surface. For example, in the case that system 200 is an inkjet web press in which the substrate may move at a relatively high speed, boundary layer 210 may have a height between 0.5 and 2.5 mm.

The air flow at boundary layer 210 may induce that satellite aerosols 114 move towards measurement area 118 and interact with corona discharge 120, which, during operation, is produced between corona source 122 and a corona ground 222.

Corona ground 222 is configured to receive charged ions originated from the corona discharge. In some examples, charged ions 214 diffuse through substrate 202 and reach corona ground 222. In the illustrated example, corona ground 222 is implemented by a conductive plate adjacent to substrate path 208 and substrate 202. Alternatively, corona ground 222 may be implemented as a plurality of grounded conductive rollers (not shown) which contact and move with substrate 202 travelling along substrate path 208. Grounded conductive rollers may be provided corresponding to a respective printhead and may be positioned in alignment with the respective printhead. Substrate 202, when travelling along substrate path 208, may be spaced from the grounded conductive plate by a distance of, for example, approximately 0.4 mm to 1 mm in order to avoid abrasion of substrate 202 and/or damage to images formed on the lower surface of substrate 202. It will be understood that this distance may vary during system operation.

In the illustrated example, corona source 122 is to generate positively charged ions 214. Ions 214 are attracted to corona ground 222. The operational voltage of corona source 122 depends on the specific environment in which examples are implemented. In a specific example in which no regulation is performed, corona source 122 may have an operational voltages of approximately 3 kV if substrate 202 contacts corona ground 222 and approximately 5-8 kV if substrate 202 is spaced approximately 0.5-1.0 mm from corona ground 222. Other arrangements are possible. During corona discharge regulation, which is illustrated below, an extra corona voltage may be applied as illustrated, as an example, in FIG. 11.

While travelling along field lines intermediate corona source 122 and corona ground 222, ions 214 encounters satellite aerosols 114. The interaction between satellite aerosols 114 and ions 214 as well as other effects such as aerosol screening of the corona voltage between source 122 and ground 222 results in a variation of corona discharge 120. This variation might be sensed by corona sensing unit 110 as described herein. In the illustrated example, corona sensing unit 110 is shown electrically connected to corona source 122 and the electrical ground. In such configuration, corona sensing unit 110 may directly sense corona current variation and, therefore, generation of satellite aerosols 114.

In some examples, corona discharge device 108 forms part of a satellite aerosol removal system configured to immobilize satellite aerosols 114 through the interaction between satellite aerosols 114 and corona discharge 120. For example, corona discharge 120 may cause a charging of satellite aerosols 114. The charged satellites are attracted to corona ground 222. In particular, the generated electrical field for corona discharge directs the electrically charged satellites downward towards corona ground 222. Thereby, the charged satellites land upon substrate 202 as shown in FIG. 2. Therefore, in some examples, a corona discharge device is operated not only to sense satellite generation but also to remove suspended satellite aerosols. Thereby, contamination of components in the fluid ejection system is prevented.

There are a variety of methods for operating a corona discharge device for immobilizing satellite aerosols, such as described in US applications with publication numbers US2012019589, US 20110051153, US20110216126. These disclosures are incorporated herein by reference in their entirety (to the extent in which this document is not inconsistent with the present disclosure) and in particular those parts thereof describing immobilization of satellite aerosols.

FIG. 3 illustrates examples herein in which the fluid ejection system is a dosing system. More specifically, FIG. 3 schematically shows a portion of a dosing system 300 including fluid ejection device 104 to eject reagent droplets 304 through nozzles 106 onto a substrate 202. Fluid droplets 110 land on desired reception regions 102 on substrate 202. Reception regions 102 may correspond to desired location on an assay plate such as a particular test well into which a desired amount of fluid is to be injected via the ejection of reagent droplets 304 from fluid ejection device 104. Fluid ejection device 104 may be constituted as a fluid jetting head built analogously as an inkjet printhead in a printing system but adapted for jetting reagent fluids.

Dosing system 300 further includes a corona discharge device comprised of a corona source 122 and a corona ground 222. In the illustrated example, as well as in other examples herein, corona ground 222 is implemented as a reference plate positioned between the corona source and the substrate. The corona discharge device in FIG. 3 also forms part of a satellite aerosol removal system configured to immobilize satellite aerosols through the interaction between satellite aerosols and the corona discharge as described above.

Looking at FIG. 3, corona source 122 includes corona wires 312, 314. Corona ground 222 is comprised of a reference plate 306. Corona wire 312 is positioned on a first side of fluid ejection device 104; corona wire 314 is positioned on a second side of fluid ejection device 104 opposite corona wire 312. Reference plate 306 is connected to ground to provide a reference for corona wires 312, 314 to operate. Reference plate 306 of FIG. 3 includes an opening 316 through which fluid droplets 304 travel to substrate 202. In the illustrated example, opening 316 is large enough to permit fluid droplets 304 to travel through without a substantial risk of impacting the sides of the opening (e.g., the reference plate 306), but is also smaller than an opening of a container in substrate 202 onto which the reagent fluid is to be disposed. As a result, opening 316 permits the fluid droplets 110 to be deposited in a specific container of substrate 202 and substantially prevents contamination of adjacent containers.

The corona discharge device is configured to implement the following two functions: a) facilitating sensing of satellite aerosols 114 generated from the ejection of droplets 108, and b) collecting or capturing satellite aerosols 114. For facilitating the implementation of these functions, in this example, dosing system 300 further includes a housing 310 that encloses a space between fluid ejection device 104 and substrate 202. During operation, satellite aerosols 114 are contained within housing 310. As satellite aerosols 114 disperse within housing 310, satellite aerosols 114 may diffuse between corona wires 312, 314 and reference plate 306. Corona wires 312, 314 generate ions 214 via a corona discharge analogously as described above with respect to FIG. 2. Ions 214 travel toward reference plate 306. Thereby, satellite aerosols 114 can interact with the corona discharge. This interaction induces changes in the corona discharge that might be sensed by corona sensing unit 110. Furthermore, ions 214 force satellite aerosols 114 toward reference plate 306. Plate 306 thereby collects satellite aerosols 114 to reduce or prevent contamination of other portions of dosing system 300 or an external environment.

During system operation, substrate 202 and/or fluid ejection device 104 move such that one of the discrete containers of substrate 202 is positioned within the fluid ejection path. When fluid ejection device 104 ejects fluid droplet(s) 304, the droplet(s) travel through opening 316 in the reference plate 306 and into the container. Dosing system 300 may pause during a settling time to permit satellite aerosols 114 within housing 310 to sufficiently disperse and be captured by corona wires 312, 314. Corona sensing unit 110 may be used to determine the settling time.

In an example, corona sensing unit 110 may be configured to monitor satellite aerosols within housing 310 after a fluid deposition for a specific container is performed. Corona sensing unit 110, or another logical component, may be further to determine when satellite aerosols within housing 310 drop below a selected aerosol level threshold. At that time, dosing system 300 may determine that the settling time is complied with and further proceed with dosing another container. After pausing, substrate 202 and/or fluid ejection device 104 moves to position another container adjacent the opening 316. In this manner, dosing system 300 efficiently captures aerosol particles resulting from fluid jetting operations.

It will be understood that the example of FIG. 3 is merely illustrative. There are a variety of dosing systems into which satellite aerosol detection might be implemented as described herein. US patent application with publication number US 2010/0282361 describes some further examples of dosing systems, which application is incorporated herein by reference in its entirety (to the extent in which this document is not inconsistent with the present disclosure) and in particular those parts thereof describing dosing systems.

Some examples herein may be specifically adapted for operation in environments with high moisture. In particular, the corona discharge device may be in particular adapted for being operational on such environments. Such examples are illustrated with respect to FIGS. 4A to 4C. These examples are contextually illustrated with respect to an inkjet web press. Such presses are designed for high productivity. Thereby, printheads are operated to eject high volume of ink towards a web moving at high speeds. Due to the high volume of ejected inks and the high speed of the web, inkjet web presses may be more prone to suffering aerosol generation. Further, costs related to downtime of inkjet web presses may be relatively high. Therefore, it is particularly advantageous being able to monitor aerosol generation in an inkjet web press as described herein. Furthermore, monitoring aerosol generation may facilitate determining condition of an inkjet web press and prevent malfunctioning by excessive aerosol generation.

FIG. 4A depicts an example of an inkjet web press 400 that includes several print bars 402 used to apply ink to a print substrate 404. Print bars 402 are disposed above a roller 406, which, during operation of press 400, holds substrate 404 in a manner that enables the application of ink(s) to print substrate 404. In the example, print substrate 404 travels over roller 406 in a direction indicated by arrows 408. As substrate 404 passes print bars 402, the print bars 402 apply different colors and/or patterns of inks to print substrate 404. With the exception(s) of the physical orientation(s), and/or the type(s) and/or color(s) of inks used by the different print bars 402, the example print bars 402 used in the web press 400 are substantially identical. Web press 400 is shown by way of example. Other configurations may be used to suit a particular application. For example, individual rollers may be used below each row of pens instead of the roller 406 to better control the spacing between the substrate and the pens.

FIG. 4B depicts a more detailed view of an example print bar 402 of web press 400 of FIG. 4A. As illustrated, print bar 402 includes multiple rows 410 and 412 of inkjet printheads and corresponding corona sources 414 and 416. In the direction of print substrate travel, corona sources 414 and 416 are disposed after or behind respective rows 410 and 412 of inkjet printheads to sense satellite aerosols emitted from the inkjet printheads. In some examples, corona sources 414 and 416 may be configured to capture satellite aerosols from the inkjet printheads. The inkjet printheads receive an ink supply from one or more ink sources 414.

Corona sources 414 and 416 are electrically connected to corona sensing unit 110 for sensing of satellite aerosol generation. Corona sensing unit 110 may be configured to sense individually each corona source, so that an assessment of aerosol generation for each inkjet printhead can be made.

Corona sources 414 and 416 may be also operated for immobilizing aerosols as described above. It will be understood that further elements may be included to operate corona sources 414. Those elements are omitted from the drawings for the sake of clarity.

FIG. 4C is a bottom view of the example print bar 402 of FIG. 4B. As depicted in this example, print bar 402 includes multiple rows 418 and 420 of inkjet printheads 410, 412. Each of corona sources 414 and 416 includes a respective corona wire 422 and 424. As depicted in FIG. 4C, corona wires 422 and 424 are only exposed in the areas that correspond to inkjet printheads 410, 412. Further, corona wires 422 and 424 are located behind their respective printheads in the direction 408 of print substrate travel shown in FIG. 4C. Where corona wires 422 and 424 are not exposed, they may be recessed in or concealed by, for example, chambers in a housing (not shown) of corona sources 414 and 416.

In the illustrated example, corona sources 414 and 416 are located behind their respective inkjet printheads 410, 412 relative to the print substrate travel path 408 to capture aerosols generated by respective ones of inkjet printheads 410, 412. In some examples, corona sources 414 and 416 may not be located immediately behind their respective inkjet printheads 410, 412 and may instead, for example, follow multiple rows of inkjet printheads.

Further examples of implementation of a corona discharge device in inkjet web presses are described in US patent application with publication number US 201110216126, which is incorporated herein by reference in its entirety (to the extent in which this document is not inconsistent with the present disclosure) and in particular those parts thereof describing implementation of corona discharge devices in inkjet web presses.

Figure 5:
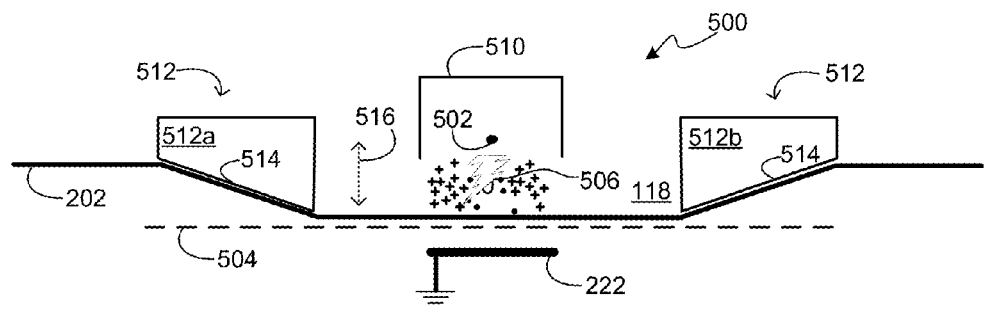
FIG. 5 shows a schematic cross-sectional view of a corona discharge device according to examples.
Figure 6:
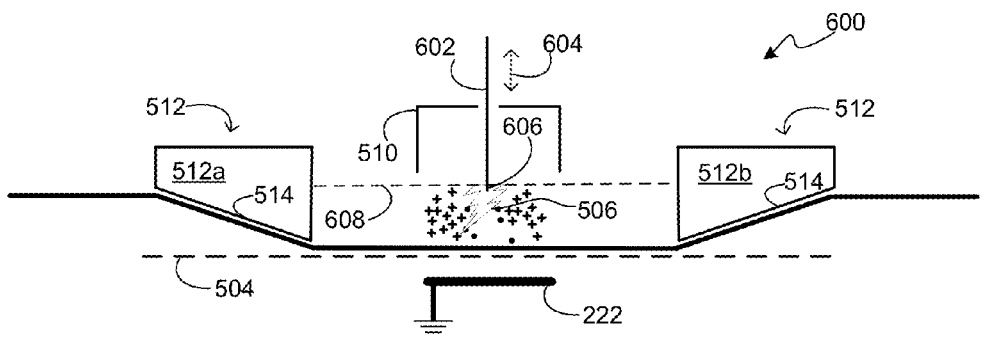
FIG. 6 shows a schematic cross-sectional view of another corona discharge device according to examples.

FIGS. 5 and 6 illustrate some specific configuration of corona discharge devices. Referring to FIG. 5, a cross sectional view of a corona discharge device 500 is illustrated. In device 500, the corona source includes a corona wire 502 to provide a corona discharge 506. Corona wire 502 is configured to extend, during system operation, along substrate 202 disposed along a substrate path 504. More specifically, corona wire 502 may extend along the substrate width. Corona discharge device 500 further includes a corona ground 222 disposed beneath a substrate location 504. Corona ground 222 may be constituted, for example, by a metal shim extending longitudinally along corona wire 502.

Corona wire 502 facilitates generation of corona discharge 506 so that satellite aerosol generation can be sensed as described herein. Since corona wire 502 extends over the substrate it facilitates that an extended area is subjected to corona discharges. Thereby it is facilitated sensing satellite aerosols over an extended area. Further, it facilitates a more consistent determination of satellite aerosol generation since sensing is averaged over the extended area.

In FIG. 5, corona wire 502 is shown, as an illustration, with a circular cross-section. The wire diameter may be, for example, between 25 to 100 μm. Typical materials for corona wire 502, and other corona sources described herein, may include tungsten. Corona wire 502 may have a length such that it extends completely or over a significant portion of the substrate width such as at least 70% or, more specifically, at least 85%.

In some examples herein, corona sources may be surrounded by a housing. Examples thereof include housing 510 of corona discharge device 500 in FIG. 5. Corona housings may be comprised of a nonconductive plastic material, such as a polyphenylene-based plastic, to prevent arcing from the high-voltage corona sources to the housing and to increase efficiency by substantially increasing the proportion of the corona current directed to the ground plane and, thereby, reducing corona current lost to surrounding system components. Further, polyphenylene-based plastics are highly resistant to water absorption. Thus, because certain environments (e.g., an inkjet press environment) may subject corona sources to humid conditions, a polyphenylene-based housing is more likely to maintain its nonconductive properties than some other materials. There are a variety of approaches for implementing corona housings. US patent application with publication number US 2011/0216126 describes further examples of corona housings, which application is incorporated herein by reference in its entirety (to the extent in which this document is not inconsistent with the present disclosure) and in particular those parts thereof describing housings for corona sources.

According to some examples, a corona discharge device includes a holding element to define the distance between a substrate and a corona source during system operation. The measurement area is then comprised of a gap between the holding element and the corona wire. For example, looking at FIG. 5, corona discharge device 500 is illustrated to include a holding element 512. Holding element 512 includes two holding sub-elements 512a, 512b disposed at opposite sides of corona wire 502. The two holding sub-elements 512a, 512b are specifically configured to hold a flexible substrate during operation of the fluid ejection system by contacting portions of the flexible substrate.

During translation of either i) a fluid ejection head to which corona discharge device is attached or ii) substrate 202, substrate 202 rides onto surfaces 514 of holding element 512 so that a gap 516 is defined between substrate 202 and corona source 502. A defined gap facilitates determining the conditions under which the corona discharge is produced. Thereby, reliability of the satellite generation sensing can be increased.

In other examples a corona source includes a corona needle that extends, during system operation, perpendicularly to a substrate onto which fluid is ejected. Such examples are illustrated with respect to FIG. 6 showing a corona discharge device 600 with a corona source including a corona wire 602 to provide corona discharge 506. The dimensions of corona needle 602 are chosen such that the corona discharge is suitable to enable satellite aerosol generation sensing. For example, corona needle 602 may have a circular cross-section with a radius at its tip smaller than 100 μm or, more specifically, between 5 to 10 μm. The tip of the corona needle may be angled (for example a sharp angle such as an angle smaller than 45 degrees). A corona needle may have different cross-sections such as, but not limited to, a circular or rectangular cross-section.

A corona generation device having a corona needle as corona source facilitates a specific spatial location of satellite aerosols sensing. Further, since the surface of the corona needle exposed to satellite aerosols is relatively low, exposure to contamination of the corona source is reduced.

Generally, the position of the corona source is chosen such that satellite aerosol sensing can be performed at a selected area. More specifically, the position of the corona source determines the spatial location of the measurement area onto which satellite aerosol sensing is to be performed. In examples in which during system operation an air flow boundary layer is formed on the substrate (see description above with respect to FIG. 2), the corona source may be positioned for sensing satellite aerosols within the boundary layer since, as set forth above, satellite aerosols may be entrained within the boundary layer. For example, corona needle 602 may be located such that, during system operation, its lower end is at a distance between 0.5 and 2.5 mm of a moving substrate generating an air flow boundary layer of such a height.

In some examples, the position of the corona sensor is adjustable in order to selectively define the location of the measurement area. More specifically, the height of a corona source with respect to the substrate might be varied. This facilitates an adjustable location of satellite aerosol sensing. For example, in systems configured such that during operation the substrate translates thereby generating an air flow boundary layer, the corona source position may be adjustable to provide a corona discharge at the boundary layer. Looking at the example of FIG. 6, the position of corona needle 602 may be adjustable along direction 604 so that its lower end 606 can be positioned within air flow boundary layer 608. Since substrate speed may be variable, it is convenient to be able to adjust the sensing location for sensing at measurement areas with a higher probability of entraining satellite aerosols.

In case corona sensing unit 118 is to quantify satellite aerosol generation, an air speed sensing device such as, but not limited to, a hot wire may be provided to facilitate measurement of air flow speed at each height where a measurement is performed. It should be understood that air speed at different heights in a boundary layer, which may correspond, at least approximately to the satellite aerosol speed, has a direct effect on the corona discharge and more specifically on the regulation parameters in a regulation process for maintaining corona current constant. For example, the same concentration of aerosols in the boundary layer at a slower speed may correspond to a higher number of charges from the corona discharge being intercepted by aerosol. Hence, a slower flow speed may convey a higher effect on the corona current. Thereby, in order to facilitate discrimination between effects of aerosol concentration and aerosol mean speed, an air speed local measurement may be convenient.

As set forth above, the corona discharge can be regulated to maintain constant corona current of the corona discharge. It will be understood that such corona discharge regulation strives to maintain the corona current close to a selected current value (i.e., a target current). However, during regulation, the corona current may present fluctuations. That is, even with corona discharge regulation, the current will be subjected to variations as illustrated further below with respect to FIG. 11. During corona discharge regulation, there might be variations of regulation parameters indicative of satellite aerosol generation. For example, a corona voltage between the corona source and a corona ground during corona discharge regulation may be monitored during regulation and used for implementing a closed-loop control of corona current. Variations of the corona voltage are indicative of satellite aerosol generation and sensing of aerosols can be based on the corona voltage. In other examples, aerosols may cause measurable current imbalances between the corona source and the corona ground during the regulation process. Variation of the current imbalances can be then used to sense satellite aerosol generation. Aerosol sensing based on current imbalances can also be used without corona discharge regulation.

Figure 7:
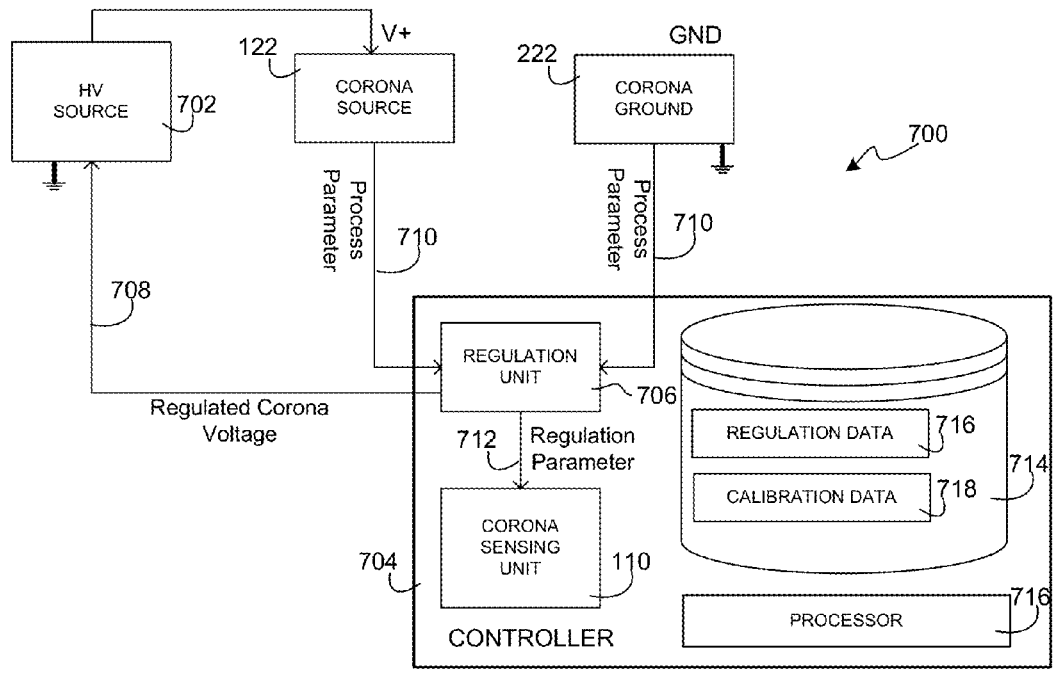
FIG. 7 shows a schematic block diagram of a fluid ejecting system according to examples.

FIG. 7 shows a schematic block diagram of a fluid ejecting system 700 implementing corona discharge regulation. System 700 is shown including corona source 122, corona ground 222, a high voltage (HV) source 702, and a controller 704. HV source 702 is electrically connected to corona source 122 for providing a positive voltage V+.

Controller 704 is illustrated including a corona sensing unit 110 and a regulation unit 706. In this example, corona sensing unit 110 represents a combination of hardware and programming to sense satellite aerosol generation. Further, regulation unit 706 represents a combination of hardware and programming to regulate corona discharge in order to maintain constant corona current of the corona discharge. In other examples, regulation unit 706 is an analog implementation of a regulating unit.

Regulation unit 706 is illustrated connected to HV source 702 in order to define a corona voltage 708. Further, regulation unit 706 is connected to corona source 122 and corona 222 for accessing process parameters 710 such as a corona current and/or a corona ground current. Regulation unit 706 may implement corona discharge regulation by executing any suitable regulation scheme that facilitates maintaining constant the corona current. (Maintaining constant the corona current may include maintaining the corona current within a selected range.) In an example, regulation unit 706 is to implement a PID controller, wherein the measured process variable is corona current or corona ground current and the desired setpoint of the controller is a target current value. In this example, the process control input to be adjusted by the controller is the corona voltage. It will be understood that there are a variety of regulations schemes that regulation unit 706 may implement to regulate corona voltage. Regulation parameters used by regulation unit 706 may be recorded in a data store 714 as part of regulation data 716.

Figure 13:
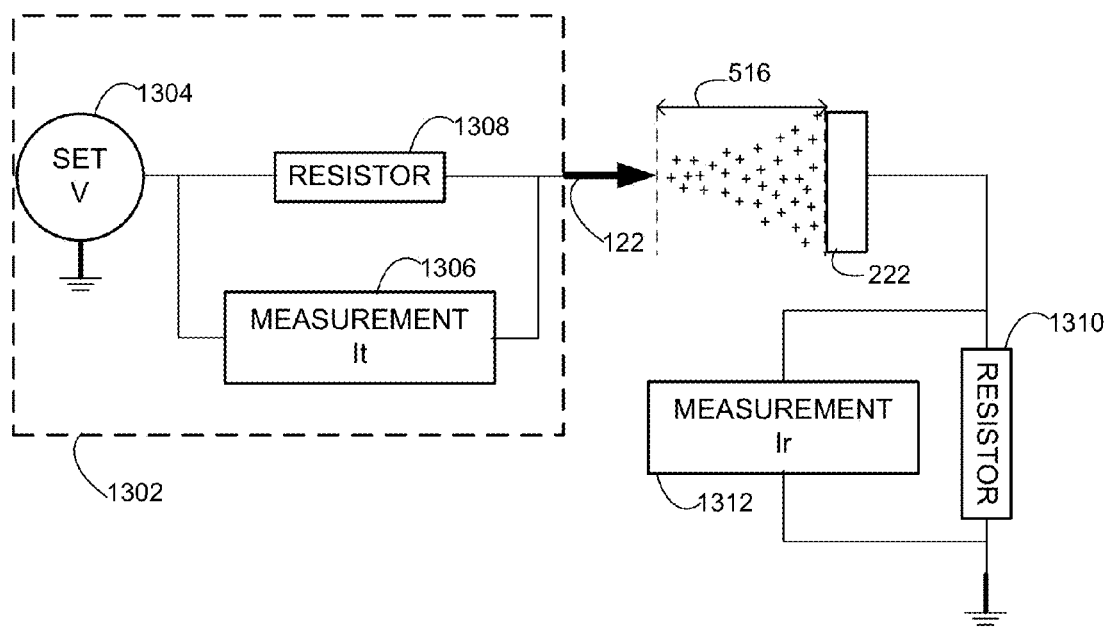
FIG. 13 shows a schematic block diagram illustrating a corona discharge regulation scheme according to examples.

A specific regulation scheme that can be implemented by regulation unit 706 is illustrated with respect to FIG. 13. In the regulation scheme of FIG. 13, corona source 122 is separated from corona ground 222 by gap 516. Corona source 122 is connected to a regulated current source 1302. Current source 1302 includes a regulable voltage supply 1304. The regulable voltage supply 1304 is isolated from corona source 122 through a resistor 1308. A current measurement device (e.g., an ammeter) 1306 is connected across resistor 1308 for measuring the total current leaving corona source 122 (i.e., current It).

Generally, in a corona device, once the geometry and environmental conditions are set, the system basically behaves according to a fixed operating curve of voltage vs. current. However, one conditions in discharge gap 516 change (e.g. the presence of an aerosol cloud, not shown in FIG. 13 but illustrated in other FIGS. 14 and 15) the operating curve changes. In other words, the interaction between aerosols and corona discharge is reflected in the change of the operating curve of the device illustrated in FIG. 13. This change can be used to make inferences about the nature of aerosol generation (i.e. amount of aerosols or location). This means, regulation parameters can be set, while the resulting value of another regulation parameter is sensed. For example, the corona voltage can be regulated via regulable voltage supply 1304 while measuring how much current flows in corona source 122 (i.e., current It) via current measurement device 1306.

In some examples, it is implemented a closed-loop control of a corona current associated with corona source 122 (i.e., current It). In such a closed-loop control, regulation unit 706 senses current It via current measurement device 1306 and makes any required changes by regulating the voltage via voltage supply 1304 to ensure that current It is maintained constant at a desired value. Corona sensing unit 110 can keep track of what voltage level is required to apply in order to maintain the target current level.

Using such a closed-loop current control, different aerosol sensing methods can be implemented as illustrated herein. Some examples, which are more specifically detailed herein, are based on corona voltage measurement and current imbalance measurement. Closed-loop control of the current results in that both corona voltage and current imbalance can be related to physical quantities associated with aerosol generation as set forth in the following.

For example, the required corona voltage to maintain corona current constant when there is an aerosol cloud in gap 516 may be higher than that required without aerosol present. This voltage increase may be somewhat proportional to the product of the amount of aerosol present times its position in the discharge gap. If the charged aerosol is close to corona ground 222, it may have a relatively low effect on the corona voltage. On the other hand, if the charged aerosol is closer to corona source 122, it may have a relatively high effect on the required corona voltage via corona screening.

In order to measure current imbalance, the regulation scheme of FIG. 13 may include a further resistor 1310 connected between corona ground 222 and the reference ground of the system. A current measurement device 1312 (e.g., an ammeter) may be connected across resistor 1310 for measuring the total current reaching corona ground 222 (i.e., current Ir). Current imbalance can be inferred based on measurement of current It and current Ir.

Figure 14:
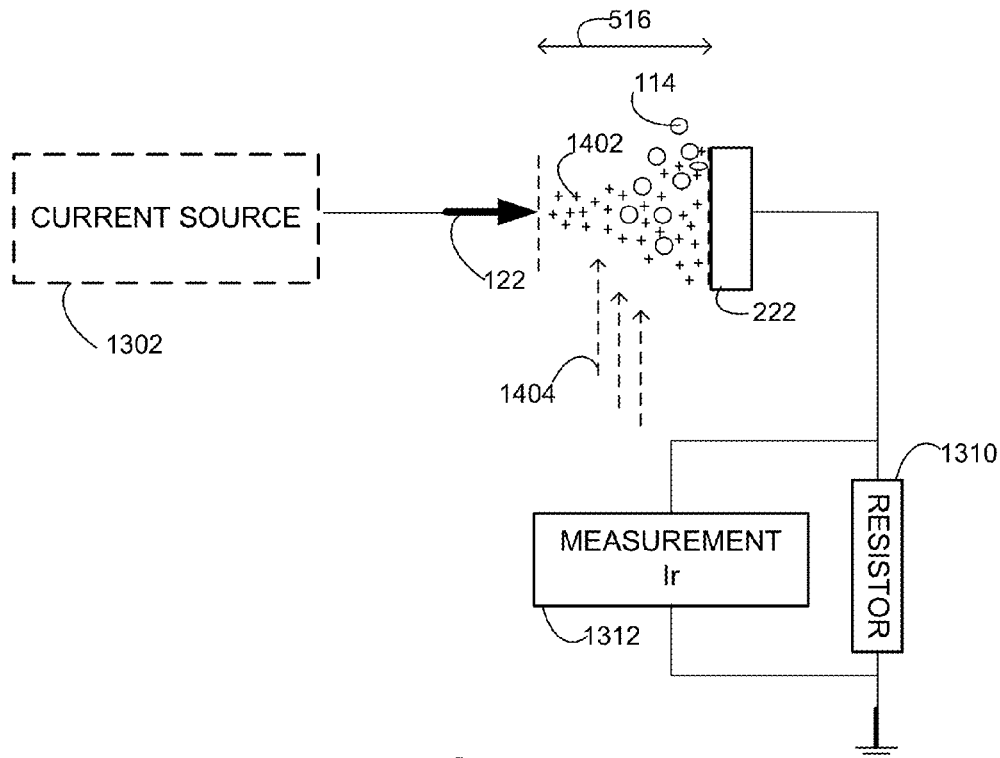
FIG. 14 shows a schematic block diagram illustrating the corona discharge regulation scheme of FIG. 13, in which satellite aerosols interact with a corona discharge according to examples.

The effect of aerosol-corona interaction on current imbalance is illustrated with respect to FIG. 14. FIG. 14 reproduces the regulation scheme of FIG. 13 in a situation in which satellite aerosols 114 interact with charges 1402 of the corona discharge. Satellite aerosols 114 are entrained in an air flow 1404, which might be generated as illustrated above (see, e.g., FIG. 2). Due to air flow 1404, satellite aerosols 114 enter in gap 516 where charges 1402 travel between corona source 122 and corona ground 222. Satellite aerosols 114 may capture a portion of charges 1404. Moreover, a portion of charged satellite aerosols may exit gap 516 before reaching corona ground 222. Thereby, a portion of the current emitted from corona source 122 may not reach corona ground 222 so that a current imbalance is created.

Therefore, the imbalance current is related to the number of charges that are intercepted by satellite aerosols and do not reach the corona ground. In principle, if the corona ground is narrow in the direction in which satellite aerosols are being transported through gap 516, current imbalance may be used to infer the number of charges intercepted by satellite aerosol. It should be understood that, generally, most of charged aerosol may not have time to land on corona ground 222 but downstream from it (satellite aerosols may move at least 300× slower than positive ions generated by a corona discharge).

Figure 15:
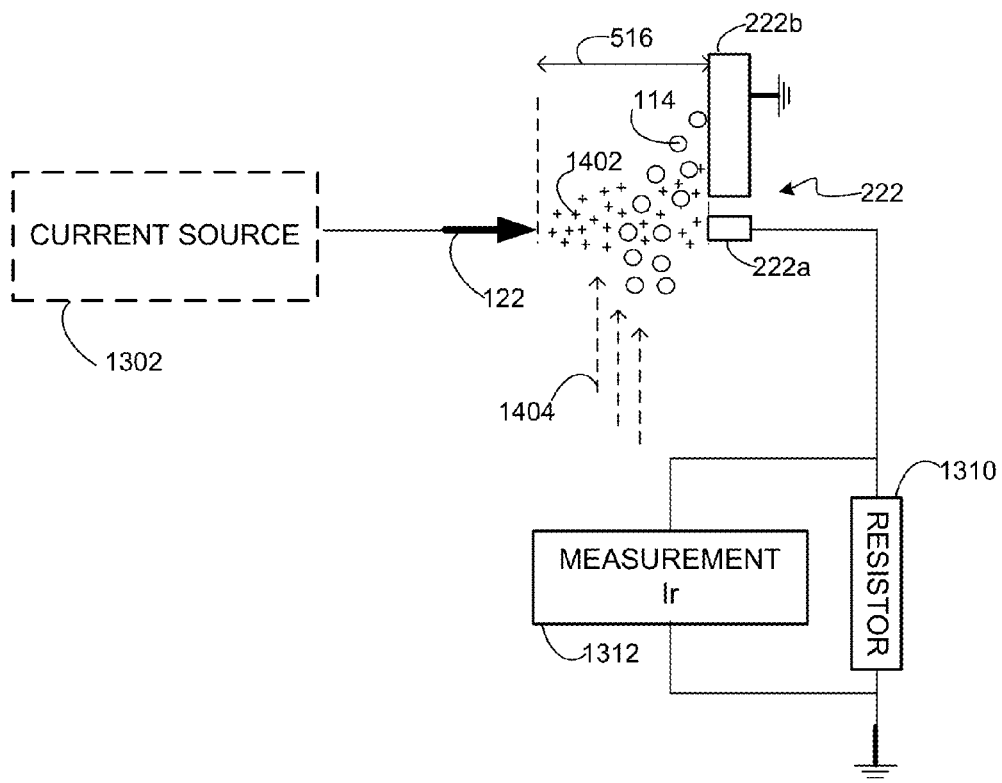
FIG. 15 shows a schematic block diagram illustrating a corona discharge regulation scheme according to other examples.

The shape and placement of corona ground 222 can be designed to improve sensibility of current imbalances to aerosol generation. For example, the corona ground may be constituted of multiple elements, each element being connected to a ground reference. Current flowing through one of the elements (i.e., a main collector) may then be monitored for sensing current imbalances as set forth above. Thereby, it is still provided a collector extension sufficient to allow charges to find a ground plane, but current is measured in a main collector for increasing sensibility of the imbalance current to aerosol generation. FIG. 15 shows a specific regulation scheme based on this principle.

In contrast to the example illustrated in FIGS. 13 and 14, in the example of FIG. 15, corona ground 222 includes two discrete portions 222a and 222b. Corona ground portion 222a is a main collector, which is connected to resistor 1310 in order to facilitate measurement of current Ir via current measurement device 1312. Corona ground portion 222b is a secondary collector, which is directly connected to a reference ground. Secondary collector 222b is provided as an extension of the corona ground to facilitate that charges find a ground plane. It will be understood that there are a variety of options for implementing a discrete corona ground. For example, the discrete corona ground may include more than two discrete portions disposed in a convenient geometrical configuration to facilitate a suitable corona discharge and a suitable current imbalance measurement. Generally, the main collector, i.e., the corona ground portion used to measure Ir, is narrower than the secondary corona portion(s) as seen from the travelling charges. In a specific example, 222, the main collector is a needle oriented parallel to the main direction of the corona discharge (e.g., parallel to corona source 122 in FIG. 14).

It should be understood that different approaches for sensing aerosols may be complementary, since each of them may provide different pieces of information that can be combined for a more accurate assessment of aerosol generation. For example, monitoring corona voltage for current monitoring may not be sufficient to quantify how much amount of aerosol or relative aerosol location in gap 516 contributes independently to the measured signal. Combining corona voltage with current imbalance facilitates modeling behavior of the aerosol. It will be understood that the exact construction of the modeling depends on the particular characteristics of the environment in which corona discharge is being implemented.

Referring back to FIG. 7, sensing unit 110 is illustrated connected to regulation unit 706 to access a regulation parameter 712. In an example, the regulation parameter is a measurement of the regulated corona voltage and sensing unit 110 is to determine the magnitude of satellite aerosol generation based on the regulated corona voltage. In another example, the regulation parameter is a corona current imbalance between the corona source and the corona ground during corona voltage regulation and sensing unit 110 is to determine the magnitude of satellite aerosol generation based on the corona current imbalance. In general, a regulation parameter is associated with a signal involved in the regulation process of the corona discharge as set forth above with respect to FIGS. 13 to 15.

Sensing unit 110 may be to determine the magnitude of satellite aerosol based on regulation parameter 712 using calibration. For example, aerosols might be delivered controllably into the measurement zones in a calibration setup. Variations of regulation parameter 712 in the calibration setup can be measured and a relationship between regulation parameter variation and magnitude of aerosol generation can be inferred. The determined relationship may be then used by sensing unit 110 during normal operation of the system for inferring, at least approximately, the magnitude of the aerosol generation. This relationship may be in the form of a semi-empirical function relating variation of the regulation parameter and aerosol generation. Alternatively, this relationship may be in the form of a look-up table (LUT) having an associative array of regulation parameter values and aerosol magnitude values. Calibration parameters used by sensing unit 110 to determine the magnitude of satellite aerosol generation may be recorded in a data store 714 as part of calibration data 718. In other examples, the relationship between aerosol regulation parameter and aerosol generation may be derived using a theoretical model of the aerosol-corona interaction.

Controller 704 is configured to execute methods described herein. Controller 704 may be implemented, for example, by one or more discrete units (or data processing components) that are not limited to any particular hardware, firmware, or software (i.e., machine readable instructions) configuration. Controller 704 may be implemented as one or more of a processor 716 and/or other structure configured to execute executable instructions including, for example, software and/or firmware instructions.

Controller 704 may be implemented in any computing or data processing environment, including in digital electronic circuitry, e.g., an application-specific integrated circuit (ASIC), a programmable digital signal processor (DSP) or in computer hardware, firmware, device driver, or software (i.e., machine readable instructions). In some implementations, the functionalities of the units are combined into a single data processing component. In other examples, the respective functionalities of each of one or more of the units are performed by a respective set of multiple data processing components. For example, in FIG. 7, regulation unit 706 and corona sensing unit 110 are illustrated separated for the sake of clarity. In examples, the functionality of regulation unit 706 and corona sensing unit 110 is implemented by the same data processing components. Controller 704 may implement further functionalities not illustrated in FIG. 7. For example, controller 704 may implement further units to control operation of a fluid ejection system as described herein.

In foregoing discussion, various components were described as combinations of hardware and programming. Such components may be implemented in a number of fashions. Referring to FIG. 8 the programming may be processor executable instructions stored on tangible memory media 802 and the hardware may include processor 716 for executing those instructions. Memory 802 can be said to store program instructions that when executed by processor 716 implements corona sensing unit 110 and regulation unit 706 of FIG. 7. Memory 802 may be integrated in the same device as processor 716 or it may be separate but accessible to that device and processor 716.

In one example, the program instructions can be part of an installation package that can be executed by processor 716 to implement corona sensing unit 110 and regulation unit 706. In this case, memory 802 may be a portable medium such as a CD, DVD, or flash drive or a memory maintained by a server from which the installation package can be downloaded and installed. In another example, the program instructions may be part of an application or applications already installed. Here, memory 802 can include integrated memory such as a hard drive.

In FIG. 8, the executable program instructions stored in memory 802 are depicted as regulation module 804 and corona sensing module 806. Regulation module 804 represents program instructions that when executed cause the implementation of regulation unit 706 of FIG. 7. Likewise, corona sensing module 806 represents program instructions that when executed cause the implementation of corona sensing unit 110. It will be understood that in examples not implementing corona regulation, memory 802 may include corona sensing module 806 and not measurement module 804.

In the following, operation of fluid ejecting systems and sensing of aerosol satellite generation are described with regard to the flow diagrams in FIGS. 9 and 10. In discussing FIGS. 9 and 10 reference is made to FIGS. 1 to 8 to provide contextual examples. Implementation however is not limited to those examples. Further, reference is also made to the diagrams in FIGS. 11 and 12. Again, such references are made simply to provide contextual examples.

FIG. 9 shows a process flow 900 for operating a fluid ejecting system (e.g., any of the fluid ejecting systems described with respect to FIGS. 1 to 4C). At block 902 a corona discharge is generated within the fluid ejection system. Controller 704 may be responsible of implementing block 902 in collaboration with a voltage source (e.g., HV source 702 in FIG. 7) connected to a corona source and a corona ground (e.g., corona source 122 and corona ground discussed above with reference to FIGS. 1 to 7). Referring to the specific example of FIG. 7, regulation unit 706 might operate HV source 702 so that the corona discharge is performed at a constant current. From the above, it will be understood that the constant current is subjected to current fluctuations resulting from, for example, interaction of satellite aerosols and the corona discharge. In other examples, the corona discharge may be generated in an unregulated manner. For example, controller 704 may operate a voltage source for setting a constant voltage between the corona source and the corona ground.

At block 904, droplets of fluids are ejected towards a reception region. Controller 704 may be responsible of implementing block 902 in collaboration with a fluid ejection device (e.g., a fluid ejection device 124 as illustrated above with respect to FIGS. 1 to 3 or the inkjet printheads in FIGS. 4A to 4C). At block 904, satellite aerosols can originate from the fluid droplets as described above.

At block 906, it is measured at least one corona discharge parameter associated with variation of the corona discharge, generated at block 902. A corona discharge parameter refers to a physical parameter associated with the corona discharge. Examples of corona discharge parameters include corona voltage or corona current (e.g., corona current or corona ground current). Corona sensing unit 110 may be responsible of implementing block 906. For example, corona sensing unit 110 may access and quantify corona current or might obtain a reading of the voltage imposed on the corona device by the voltage source. In examples in which corona discharge is regulated (e.g. closed-loop control of corona current), corona sensing unit 110 might obtain the corona discharge parameter as a regulation parameter from regulation unit 706. In the latter examples, the at least one corona discharge parameter is measured during corona discharge regulation. For example, the at least one corona discharge parameter may include a corona voltage and/or corona current imbalance between the corona source and the corona ground during corona voltage regulation as described with respect to FIGS. 11 to 15.

At block 908, the magnitude of satellite aerosol generation from the fluid droplets on the measured at least one corona discharge parameter is determined. Corona sensing unit 110 may be responsible of implementing block 908. Therefore, corona sensing unit 110 may associate measured values of the corona discharge parameter with magnitude of satellite aerosol generation using a calibration setup as described with respect to FIG. 7.

Process flow 900 may further include causing a corona generation discharge such that satellite aerosols are immobilized. Controller 704 may be responsible of implementing this function. In principle, whether or not satellite aerosols are immobilized when entering in an area where corona discharge is being produced (e.g., measurement area 118 in FIGS. 1 to 3) depends on the corona voltage. It will be understood that the corona voltages for aerosol immobilization depends on the specific application and more particularly, of the characteristic of the system and satellite aerosols to be immobilized.

FIG. 10 shows a process flow 1000 for sensing aerosols according to examples. FIG. 10 is illustrated referring to FIG. 1. Process flow 1000 may be performed within a printing system (e.g., printing system 200, 400 in FIGS. 2 and 4) including an inkjet printhead to eject droplets of ink. During operation of such printing systems and as set forth above, aerosols can originate as satellite aerosols from the ink droplets. The sensing implemented by process flow may include determining magnitude of aerosol satellite aerosol generation caused by the inkjet printhead based on the interaction between satellite aerosols and the corona discharge. Process flow 1000 may be implemented in other fluid ejection systems such as, but not limited to, dosing system 200 in FIG. 2. Further, process flow 1000 may be implemented for any system and/or environment in which aerosol particles are generated.

At block 1002, corona discharge 120 is generated in measurement area 118 by imposing a corona voltage between corona source 122 and a corona ground (e.g., corona ground 222 in FIG. 2 or 3). Controller 704 may be responsible of implementing block 902 in collaboration with a voltage source (e.g., HV source 702 in FIG. 7) connected to the corona source and the corona ground.

In some examples, process flow 1000 may include generating an air flow that induces aerosol particles to enter into the measurement area. Aerosols entering into measurement area 118 can interact with the corona discharge. There are multiple mechanisms that may produce the air flow. For examples, in a printer implementation in which the substrate translates during printing (e.g., an inkjet web press) controller 704 may cause translation of the substrate. As set forth above with respect to FIGS. 2 and 6, substrate translation may engender a boundary layer of air flow contiguous to the substrate. The air flow induces that satellite aerosols are entrained in the boundary layer and enters measurement area 118. In other examples, the air flow might be generated by a dedicated device. For example, a ventilator (e.g., formed by a rotating disc) might be provided and operated to purposively generate such air flow.

At block 1004, the corona discharge is regulated to maintain constant corona current. Looking at FIG. 7, regulation unit 706 might operate HV source 702 to maintain the corona discharge at a constant current. The following pseudo code illustrates a method that regulation unit 706 might implement for regulating corona voltage to maintain corona current (It) at a constant target current.

| | |
|---|---|
| 100 | measure corona current (It) |
| 110 | IF It < target current THEN increase corona voltage |
| 120 | IF It > target current THEN decrease corona voltage |
| 130 | GOTO 100 |

Target current might be selected such that the corona discharge induces that satellite aerosols are immobilized as described above.

At block 1006, aerosols in measurement area 118 may be sensed based on a regulation parameter (e.g., corona voltage, current fluctuations, and/or current imbalance). As further described below with respect to FIG. 11, the regulation parameter is affected by the interaction between satellite aerosols and the corona discharge.

Corona discharge regulation and aerosol sensing is illustrated in more detail in the following with respect to FIG. 11. As set forth above, a corona discharge may be regulated in a current control mode for maintaining constant the corona current. When satellite aerosols are in the measurement area in which the corona discharge is being produced, the satellite aerosols may carry off some of the charges. Further, at the same time the charged aerosols may also screen the corona voltage. Both phenomena results in a fluctuation of the corona current. The regulation mechanism reacts to the current fluctuation by raising the corona voltage to maintain corona current at the target current.

Generally, the variation of the corona voltage for reacting to the current decrease is, at least approximately, directly proportional to the aerosol surface area. In some applications, the aerosol surface area may be the key quantity sought after. Generally, the aerosol surface area is a function of the particle count. Therefore, regulating parameters may be used to sense and quantify aerosol generation. This detection method is suited also for high aerosol concentrations such as, for example, a concentration between $10^3$ and $10^6$ particles per $cm^3$. This detection method is also effective at aerosol densities where other convention aerosol detection methods (e.g., laser detection) require particle dilution for being effective, such as a concentration above $10^4$ particles per $cm^3$.

As set forth above with respect to FIGS. 13 to 15, a further regulation parameter that may be used to sense and quantify aerosol generation is current imbalance between a corona source and a corona ground. As set forth above, interaction between satellite aerosols and free charges from the corona discharge may result in charging of satellite aerosols. In other words, charges from the corona discharge may be transferred to satellite aerosols. Without interaction with satellite aerosols, the current flowing through the corona source and the corona ground is the same (i.e., all free charges emitted from the source reach the ground). However, when charged satellite aerosols are created, current imbalance may originate if the ground plane is relatively short in the motion direction of charged satellite aerosols. Thereby, charged satellite aerosols may not land on the ground plane. (It should be taken into account that mobility of charged satellite aerosols is generally smaller than that of the free charges.) Therefore, interaction between satellite aerosols and corona discharge may decrease the current flowing through the corona ground and, hence, result in a current imbalance.

The effect of interaction between satellite aerosols and corona discharge on regulation parameters is reflected in FIG. 11. FIG. 11 is a graph 1100 showing variation over time (indicated at bottom axis 1114) of various regulation parameters. Data corresponds to a system in which a corona ground is positioned beneath a translating substrate (in this example, a moving web). The corona source in this example corresponds to a corona wire similar as illustrated with respect to FIGS. 4A to 4C. There is a 3 mm gap present between the corona wire and the substrate including the measurement area. In such a system both a corona current 1102 and a corona ground current 1104 can be measured. Current values are indicated on right side axis 1106. Graph 1100 further includes corona wire voltage 1108 and power supply voltage 1110. (Power supply voltage may be read, for example, by isolating the power supply from the corona source with a resistor as illustrated above with respect to FIG. 13.) Voltage values are indicated on left side axis 1106. The system is operated with a corona discharge regulation for maintaining corona current 1102 at a target current of approximately 200 μA.

Initially, between $t_0$ and $t_1$, there is no aerosol going through the measurement area. At a time of about 300 sec ($t_1$) ink jet printing starts and so does aerosol start to be generated and dragged into the gap by the drag flow created by the substrate moving at 2 m/s. As soon as the aerosol flows into the measurement area, it interacts with the corona discharge. For example, aerosol may start to be charged by the corona discharge and/or generate a screening potential that results in a fluctuation of the corona current. Corona discharge regulation reacts to the corona current fluctuation by raising the voltage imposed on the corona source. This is reflected in the rise of corona source voltage 1108 and power supply voltage 1110 after instant $t_1$.

Current imbalance can also be observed in graph 1100. In particular, it can be observed in the curve corresponding to corona ground current 1104 that the amount of current reaching the corona ground diminishes as some of the charged aerosol does not have time to descend onto the corona ground.

Graph 1100 therefore illustrates the feasibility of using corona voltage and/or current imbalance for aerosol sensing. Further, using calibration methods as described above, satellite aerosol generation may be quantified from the voltage values.

Referring back to FIGS. 9 and 10, process flows 900 and 1000 may further include blocks for reacting to sensed aerosols. For example, if the sensed aerosols are above a selected threshold level, a signal can be sent to monitoring system that performs a predetermined action such as signaling a system operator or causing the involver system to stop. Further, quantification of sensed aerosols may be used to monitoring condition of fluid ejection systems. For example, aerosol generation of a system may be monitored during system lifetime. When the accumulated sensed aerosols are above a certain level, a serviceable condition of the system may be signaled. At that condition, a system operator might service the system for checking whether aerosol generation has caused some system damage or malfunctioning.

Further, process flows 900 and 1000 may further include blocks for adjusting the corona discharge such that aerosol immobilization can be effected by the aerosol discharge. Aerosol immobilization is discussed above.

As set forth above, one of the mechanisms that may be exploited for sensing satellite aerosol generation is the aerosol screening potential created between the corona source and the corona ground. This is illustrated by way of example with respect to FIG. 12. FIG. 12 shows a graph 1200 showing theoretical curves 1202*a*-1202*c* that relate the percentage of area covered by the aerosol (also referred to as aerosol screening cross-section) and the screening potential in Volts for different corona currents densities. Curve 1206*a* corresponds to a corona current density of 0.5 μA/cm; curve 1206*b* corresponds to a corona current density of 1 μA/cm; curve 1206*c* corresponds to a corona current density of 2 μA/cm. As can be seen from the graph, there is aerosol-corona interaction can be modeled a linear relationship between the screening potential and the aerosol screening cross-section, which is directly directed to the number of aerosol particles interacting with the corona discharge. The curves are derived for an aerosol layer at 1 mm height over the corona ground.

In the foregoing description, numerous details are set forth to provide an understanding of the examples disclosed herein. However, it will be understood that the examples may be practiced without these details. While a limited number of examples have been disclosed, numerous modifications and variations therefrom are contemplated. It is intended that the appended claims cover such modifications and variations. Claims reciting "a" or "an" with respect to a particular element contemplate incorporation of one or more such elements, neither requiring nor excluding two or more such elements. Further, the terms "include" and "comprise" are used as open-ended transitions.

What is claimed is:

1. A system for ejecting a fluid on a reception region, the system comprising:

a fluid ejection device including a plurality of nozzles to eject droplets of the fluid towards the reception region, whereby, during system operation, satellite aerosols can originate from the fluid droplets;

a corona discharge device to provide a corona discharge from a corona source; and a sensing unit to sense satellite aerosol generation caused by the fluid ejection device based on the interaction between satellite aerosols and the corona discharge.

2. The system of claim 1, wherein the system is a printing system for printing an image pattern on a substrate, the fluid including ink and the fluid ejection device including an inkjet printhead to eject droplets of ink onto the substrate for forming the image pattern, during operation of the printing system, a portion of the substrate being positioned on the reception region.

3. The system according to claim 2, wherein the corona discharge device is to provide a corona discharge at a measurement area, which measurement area, during system operation, is at a boundary layer of air flow contiguous to the substrate.

4. The system according to claim 3, wherein the system is to generate the air flow by translating the substrate during printing, the air flow inducing satellite aerosols movement towards the measurement area.

5. The system according to claim 2, wherein the corona discharge device further includes a holding element to define the distance between the substrate and the corona source during system operation, the corona discharge device being to provide the corona discharge at a gap formed between the holding element and the corona wire.

6. The system according to claim 1, wherein the corona source includes a corona wire, the corona wire extending, during system operation, along a substrate onto which fluid is ejected.

7. The system according to claim 1, wherein the corona source includes a corona needle, the corona needle extending, during system operation, perpendicularly to a substrate onto which fluid is ejected.

8. The system according to claim 1, further comprising a corona regulation unit to maintain constant corona current of the corona discharge.

9. The system according to claim 8, wherein the sensing unit is further to determine the magnitude of satellite aerosol generation based on a corona voltage between the corona source and a corona ground during corona discharge regulation.

10. The system according to claim 8, wherein the sensing unit is further to determine the magnitude of satellite aerosol generation based on a corona current imbalance between the corona source and the corona ground during corona discharge regulation.

11. The system according to claim 1, wherein the corona discharge device forms part of a satellite aerosol removal system configured to immobilize satellite aerosols through the interaction between satellite aerosols and the corona discharge.

12. A computer software product comprising a tangible medium readable by a processor, the medium having stored thereon a set of instructions for operating a fluid ejection system, the fluid ejection system being for ejecting a fluid on a reception region, the instructions including:

a set of instructions which, when loaded into a memory and executed by the processor, causes generation of a corona discharge within the fluid ejection system;

a set of instructions which, when loaded into a memory and executed by the processor, causes the fluid ejection system to eject droplets of the fluid towards a reception region, whereby, satellite aerosols can originate from the fluid droplets;

a set of instructions which, when loaded into a memory and executed by the processor, causes measuring at least one corona discharge parameter associated with variation of the corona discharge; and a set of instructions which, when loaded into a memory and executed by the processor, causes determining magnitude of satellite aerosol generation from the fluid droplets on the measured at least one corona discharge parameter.

13. The product of claim 12, wherein the instructions further include a set of instructions which, when loaded into a memory and executed by the processor, implements a closed-loop control of a corona current associated with the corona discharge, the at least one corona discharge parameter being measured during closed-loop control of the corona current.

14. The product of claim 13, wherein the measured at least one corona discharge parameter includes a corona voltage being measured during control of the corona current.

15. The product of claim 13, wherein the measured at least one corona discharge parameter includes corona current imbalance between the corona source and a corona ground measured during control of the corona current.

16. The product of claim 12, wherein the instructions further include a set of instructions which, when loaded into a memory and executed by the processor, causes adjustment of the position of the corona source in order to selectively define the location where magnitude of satellite aerosol generation is determined.

17. A method of sensing aerosols, the method comprising:
generating a corona discharge in a measurement area by imposing a corona voltage between a corona source and a corona ground;

regulating the corona discharge to maintain constant corona current; and sensing aerosols in the measurement area based on a regulation parameter, the regulation parameter being affected by the interaction between satellite aerosols and the corona discharge.

18. The method according to claim 17, wherein the regulation parameter used to sense aerosols is a corona voltage between the corona source and the corona ground during corona discharge regulation.

19. The method according to claim 17, wherein the regulation parameter used to sense aerosols is a corona current imbalance between the corona source and the corona ground during corona discharge regulation.

20. The method of claim 17, wherein the method is performed within a printing system including an inkjet printhead to eject droplets of ink, whereby during system operation, aerosols can originate as satellite aerosols from the ink droplets, the sensing including determining magnitude of aerosol satellite aerosol generation caused by the inkjet printhead based on the interaction between aerosol satellite aerosol and the corona discharge.

* * * * *